US009566471B2

(12) United States Patent
DeAngelis et al.

(10) Patent No.: US 9,566,471 B2
(45) Date of Patent: Feb. 14, 2017

(54) SYSTEM AND METHODS FOR PROVIDING PERFORMANCE FEEDBACK

(75) Inventors: Douglas J. DeAngelis, Ipswich, MA (US); Edward G. Evansen, Walpole, MA (US)

(73) Assignee: ISOLYNX, LLC, Haverhill, MA (US)

( * ) Notice: Subject to any disclaimer, the term of this patent is extended or adjusted under 35 U.S.C. 154(b) by 770 days.

(21) Appl. No.: 13/231,802

(22) Filed: Sep. 13, 2011

(65) Prior Publication Data

US 2012/0081531 A1 Apr. 5, 2012

Related U.S. Application Data

(63) Continuation of application No. PCT/US2010/027349, filed on Mar. 15, 2010.
(Continued)

(51) Int. Cl.
*A63B 24/00* (2006.01)
*G06F 19/00* (2011.01)

(52) U.S. Cl.
CPC ....... *A63B 24/0021* (2013.01); *G06F 19/3481* (2013.01); *A63B 24/0062* (2013.01);
(Continued)

(58) Field of Classification Search
CPC ............ A63B 24/0021; A63B 2243/007; A63B 2024/0012; A63B 2024/0025; A63B 2024/0056; A63B 2024/0065; A63B 2220/12; A63B 2220/17; A63B 2220/20; A63B 2220/30; A63B 2220/40; A63B 2220/806; A63B 2225/15; A63B 2225/50; A63B 24/0006; A63B 24/0084; A63B 69/0028; A63B 24/0062; A63B 2024/0009; A63B 2071/0625; A63B 2071/063; A63B 2220/14; A63B 2220/18; G01C 22/00; G01S 5/0027; G01S 19/19; G01S 19/36; G07C 1/24; Y10S 482/902; A61B 1/041; A61B 1/00036; A61B 1/0005; A61B 19/52; H04N 7/18
See application file for complete search history.

(56) References Cited

U.S. PATENT DOCUMENTS 4,775,151 A 10/1988 Berry
4,776,323 A 10/1988 Spector
(Continued)

FOREIGN PATENT DOCUMENTS

JP 10206180 A * 8/1998
WO 9805977 A1 2/1998
(Continued)

OTHER PUBLICATIONS

English Machine Translation Takashima (JP 10-206180).*
(Continued)

*Primary Examiner* — Mohammed Jebari
(74) *Attorney, Agent, or Firm* — Lathrop & Gage LLP

(57) ABSTRACT

Systems and methods provide feedback to at least one participant in a field of play. A performance analysis device determines performance information of each participant in the field of play, where the performance information is based upon at least one of determined location, speed, path, acceleration and biometrics of said each participant. At least one output device provides real-time feedback to the at least one participant based upon the performance information. The real-time feedback comprises performance information of the at least one participant and/or performance information of one or more other participants in the field of play.

23 Claims, 4 Drawing Sheets

Related U.S. Application Data

(60) Provisional application No. 61/160,141, filed on Mar. 13, 2009.

(52) U.S. Cl.
CPC .......... *A63B 2024/0012* (2013.01); *A63B 2024/0025* (2013.01); *A63B 2024/0056* (2013.01); *A63B 2024/0065* (2013.01); *A63B 2220/12* (2013.01); *A63B 2220/17* (2013.01); *A63B 2220/20* (2013.01); *A63B 2220/30* (2013.01); *A63B 2220/40* (2013.01); *A63B 2220/806* (2013.01); *A63B 2225/15* (2013.01); *A63B 2225/50* (2013.01); *A63B 2230/06* (2013.01); *A63B 2230/202* (2013.01); *A63B 2230/207* (2013.01); *A63B 2230/42* (2013.01); *A63B 2230/50* (2013.01); *A63B 2243/007* (2013.01); *A63B 2243/0025* (2013.01)

(56) References Cited

U.S. PATENT DOCUMENTS

| | | | |
|---|---|---|---|
| 5,697,791 A | | 12/1997 | Nashner et al. |
| 5,710,894 A | * | 1/1998 | Maulsby et al. .............. 715/763 |
| 6,013,007 A | * | 1/2000 | Root et al. .................... 482/8 |
| 6,220,865 B1 | * | 4/2001 | Macri et al. .................. 434/247 |
| 6,605,046 B1 | | 8/2003 | Del Mar |
| 6,661,342 B2 | | 12/2003 | Hall |
| 6,710,713 B1 | | 3/2004 | Russo |
| 6,736,759 B1 | * | 5/2004 | Stubbs et al. ................ 482/8 |
| 6,868,338 B1 | * | 3/2005 | Elliott .......................... 701/469 |
| 6,882,315 B2 | | 4/2005 | Richley et al. |
| 6,998,987 B2 | | 2/2006 | Lin |
| 7,062,895 B1 | * | 6/2006 | Sperie ........................... 54/71 |
| 7,511,604 B2 | | 3/2009 | Raphaeli et al. |
| 7,667,604 B2 | | 2/2010 | Ebert et al. |
| 7,671,802 B2 | | 3/2010 | Walsh et al. |
| 7,710,322 B1 | | 5/2010 | Ameti et al. |
| 7,969,348 B2 | | 6/2011 | Baker et al. |
| 8,169,319 B2 | | 5/2012 | Kaplan et al. |
| 8,368,721 B2 | * | 2/2013 | McCoy ......................... 345/633 |
| 8,457,392 B2 | | 6/2013 | Cavallaro et al. |
| 8,768,343 B2 | | 7/2014 | Wisherd |
| 8,842,002 B2 | | 9/2014 | Rado |
| 2002/0041284 A1 | | 4/2002 | Konishi et al. |
| 2002/0116147 A1 | | 8/2002 | Vock et al. |
| 2003/0095186 A1 | | 5/2003 | Aman et al. |
| 2003/0125138 A1 | * | 7/2003 | John et al. .................... 473/415 |
| 2003/0163287 A1 | | 8/2003 | Vock |
| 2003/0227453 A1 | | 12/2003 | Beier et al. |
| 2004/0006424 A1 | | 1/2004 | Joyce |
| 2004/0178955 A1 | | 9/2004 | Menache |
| 2005/0207617 A1 | | 9/2005 | Sarnoff |
| 2006/0032315 A1 | * | 2/2006 | Saalastic ................ A61B 5/222, 73/808 |
| 2006/0152303 A1 | | 7/2006 | Liang |
| 2006/0160488 A1 | | 7/2006 | Sueoka |
| 2006/0281061 A1 | | 12/2006 | Hightower et al. |
| 2007/0032143 A1 | * | 2/2007 | Short ........................... 440/2 |
| 2007/0126558 A1 | | 6/2007 | Donato |
| 2008/0015089 A1 | * | 1/2008 | Hurwitz et al. .................. 482/8 |
| 2008/0140233 A1 | | 6/2008 | Seacat |
| 2008/0221745 A1 | * | 9/2008 | Diamandis et al. ............. 701/3 |
| 2008/0234077 A1 | * | 9/2008 | Glowinski .................... 473/570 |
| 2008/0249736 A1 | * | 10/2008 | Prstojevich .................. 702/141 |
| 2008/0312010 A1 | * | 12/2008 | Marty et al. .................. 473/447 |
| 2009/0048039 A1 | | 2/2009 | Holthouse |
| 2009/0079580 A1 | | 3/2009 | Kaplan et al. |
| 2009/0231198 A1 | | 9/2009 | Walsh et al. |
| 2010/0026809 A1 | | 2/2010 | Curry |
| 2010/0184563 A1 | | 7/2010 | Molyneux |
| 2010/0283630 A1 | | 11/2010 | Alonso |
| 2011/0205022 A1 | | 8/2011 | Cavallaro |

FOREIGN PATENT DOCUMENTS

| | | | |
|---|---|---|---|
| WO | WO 01/00281 | * | 1/2001 |
| WO | WO 01/08417 A1 | | 2/2001 |
| WO | WO2014/197600 A1 | | 12/2014 |

OTHER PUBLICATIONS

International Search Report and Written Opinion issued in related PCT Patent Application PCT/US10/27349, issued May 17, 2010, 12 pages.

Response to Written Opinion issued in related PCT Patent Application PCT/US10/27349, filed Jan. 13, 2011, 31 pages.

International Preliminary Report on Patentability issued in related PCT Patent Application PCT/US10/27349, issued Sep. 7, 2011, 22 pages.

Canadian Patent Application 2,755,401 Examiner's Report dated Jan. 12, 2016, 3 pages.

IsoLynx Real-Time Player Tracking & Game Analysis Technology (2010), available at http://web.archive.org/web/20100604012151/http://www.finishlynx.com/isolynx/.

InMotio—Tactical, Training and Performance Management video (available at https://www.youtube.com/watch?v=dq1n7IYePJI).

Fraunhofer IIS 2010 Annual Report at 83 (available at http://www.eas.iis.fraunhofer.de/content/dam/eas/de/documents/jahresbericht/JB10_en_gl_low_res_tcm182-91049.pdf.

Zebra Intros Next-Gen RTLS Leveraging Ultra-Wideband Technology, RFID Journal available at http://www.rfidjournal.com/articles/view?7889.

\* cited by examiner

_US 9,566,471 B2_

SYSTEM AND METHODS FOR PROVIDING PERFORMANCE FEEDBACK

RELATED APPLICATIONS

This application is a continuation of PCT Patent Application Serial No. PCT/US2010/027349, filed Mar. 15, 2010 which claims priority to U.S. Patent Application Ser. No. 61/160,141, filed Mar. 13, 2009, all of which are incorporated herein by reference.

BACKGROUND

Traditionally, video and still images of a live event (i.e., video content and still image content) are created by a team of professionals. In the case of video content, highly trained camera persons operate one or more cameras and highly trained production staff operate production equipment (e.g., within a production van at a sporting event) to select camera shots and combine graphics into a production feed. In the case of still image content, highly skilled camera persons operate still cameras to capture still images of an event and submit these still images to one or more editors who select shots for use in magazines, for example.

The cost of producing video and still image content defines the market size required to cover this cost. Thus, only events having a sufficient market justify the cost of producing video and still image content. Although technology has reduced the cost of production, the cost of skilled human operators remains high.

Images from a camera may be used to visually track an object (e.g., a golf ball) within the camera's field of view. The camera may be motorized to allow it to move so as to maintain the moving object within its field of view. However, such systems fail when the camera 'loses sight' of the object; for example, the camera may lose sight of the object if the object becomes visually obscured by another object.

For certain sporting events, cameras may be motorized to facilitate tracking of competitors and are operated by remote camera operator. These cameras still require the skill of a person.

Many systems have been developed to track objects by attaching a sensor to the object and then using the sensor to determine the location of the object. Such object tracking provides data (e.g., speed) to computer systems but is not known to facilitate real image production.

SUMMARY

In an embodiment, a system provides feedback to one or more participants in a field of play. The system includes a performance analysis device for determining performance information of each participant in the field of play. The performance information is based upon at least one of determined location, speed, path, acceleration and biometrics of the participant. The system also includes at least one output device for providing real-time feedback to the participants based upon the performance information.

In another embodiment, a system provides feedback to a leader of one or more participants in a field of play. The system includes a performance analysis device for determining performance information of each of the participants, where the performance information is based upon at least one of determined location, speed, path, acceleration and biometrics of said each participant. The system also includes an output device for providing real-time feedback to the leader based upon the performance information.

In another embodiment, a method provides feedback to at least one participant in a field of play. Successive locations of the participant within an operational field are determined. Performance of the participant is determined based upon the successive locations, real-time feedback is provided to the participant based upon the determined performance.

In another embodiment, a system provides feedback to at least one participant in a field of play. The system includes a performance analysis device for determining performance information of each participant in the field of play, where the performance information is based upon at least one of determined location, speed, path, acceleration and biometrics of said each participant. The system also includes at least one output device for providing real-time feedback to the at least one participant based upon the performance information.

DETAILED DESCRIPTION OF DRAWINGS

Figure 1:
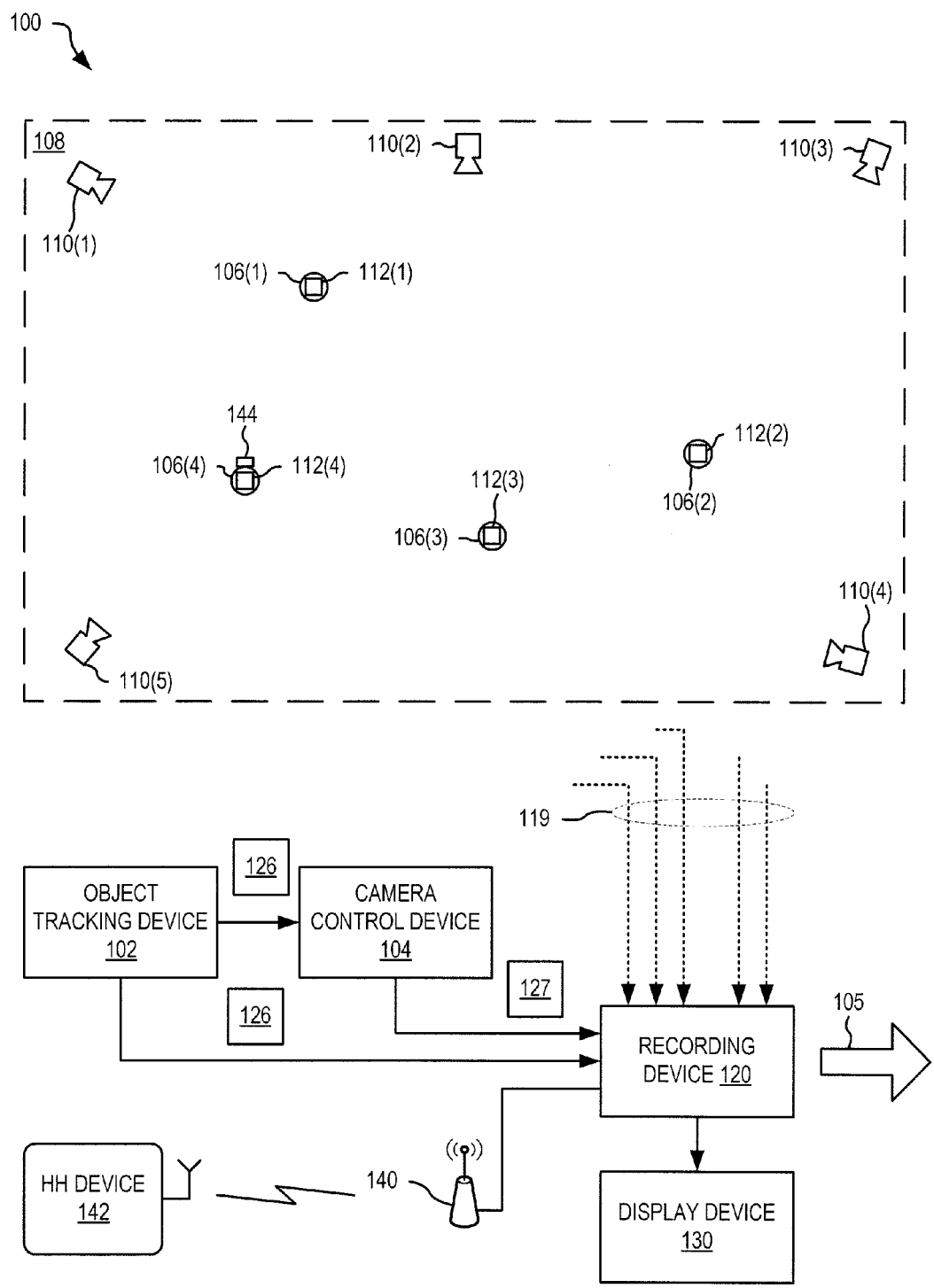
FIG. 1 shows one exemplary system for capturing performance data of tracked objects moving within an operational field, in an embodiment.

FIG. 1 shows one exemplary use of a system 100 for capturing performance data of tracked objects 106 moving within an operational field 108. Objects 106 for example represent runners, football players, speed skaters, race cars or horses and/or jockeys, and field 108 represents a running track, a football field, an ice rink, a race track or a horse track, respectively.

System 100 is shown with an object tracking device 102, a recording device 120, a display device 130, an optional camera control device 104 and five optional motorized cameras 110. If included, cameras 110 may be situated within or around operational field 108. Four exemplary objects 106 are shown within field 108, each object having a location unit 112.

Object tracking device 102 utilizes location units 112 to determine location information (e.g., coordinate data) for objects 106 within operational field 108. Object tracking device 102 sends this location information to recording device 120 and optionally to camera control device 104. Camera control device 104 may include a model of operational field 108, with coordinates of each camera 110. Camera control device 104 receives coordinate data of objects 106 from object tracking device 102, determines a possible field of view from each camera 110 to each object 106, and assigns cameras 110 to the objects based upon optimum field of view selection. For example, for each camera 110 and for each object 106, camera control device 106 determines a possible field of view from the camera to the object. Then, by selecting an optimum field of view for each object (e.g., based upon the distance from the camera to the object, the objects position within field 108 and whether all objects are assigned to a camera), control device 104 determines which camera 110 to assign to each object 106. Where the number of objects is less that the number of cameras, camera control device 104 may assign more than one camera 110 to an object 106. Where the number of objects is more than the number of cameras, camera control device 104 may assign one or more select cameras 110 to a more important object 106 (e.g., the leader in a race). Each object 106 is for example prioritized such that cameras assignment is also prioritized for that object—in a race, the leader is assigned a higher priority to ensure best camera assignment.

As objects 106 move within field 108, object tracking device 102 may provide, for each object 106, velocity and position information 126 to recording device 120 and to camera control device 104. Camera control device 104 uses this velocity and position information for optimal camera assignment to each object 106. Thus, camera control device 104 may be made aware of movement characteristics (e.g., direction of movement) of objects 106, and accordingly assigns or re-assigns cameras based upon camera fields of view that include the front of object 106. Further, camera control device 104 for example assumes that the front of object 106 faces forward as it moves, or it may instead be programmed to identify the front of object 106 as the aspect facing the general direction of movement of an event. Camera control device 104 accordingly assigns and controls cameras 110 to capture frontal and side image data of object 106, in preference to rear images.

Recording device 120 records velocity and positional information 126 received from object tracking device 102 and may record and/or convert image data 119 from each camera 110. Camera control device 104 may also provide annotation data 127 to recording device 120 such that recording device 120 may record relevant camera information (e.g., zoom, direction and azimuth) with velocity and positional information 126.

In one embodiment, recording device 120 simultaneously records image data 119 from each camera 110, velocity and position information 126 and annotation data 127. Image data 119 is a signal or signals representing data bits captured by each camera 110. Recording device 120 includes processing software for converting the received signal into a data stream and interpreting the data stream as a series of images, which are then recorded as video, for example. System 100 is thus suitable for use in autonomous still or moving picture production.

Camera control device 104 sends annotation data 127 to recording device 120 for recording with image data 119. Annotation data 127 includes identification of tracked objects of image data 119. For example, if camera 110(1) is selected to maintain object 106(1) within its field of view, as the image data from camera 110(1) is recorded by recording device 120, camera control device 104 may include identification of object 106(1) within annotation data 127 that is recorded with the image data.

Recording device 120 may generate a live feed 105 (optionally including annotation data and performance characteristics of displayed objects) and allow interaction with a user through display device 130.

Recording device 120 may display images from selected cameras 110 on display device 130 together with measured performance statistics.

Recording device 120 may include additional functionality for determining performance statistics and movements of objects 106. In one example, recording device 120 shows a plan view of at least part of field 108 on display 130 and plots movement of objects 106 over select periods. Recording device 120 may also determine performance data for objects 106 and include this performance data, e.g., as a video overlay, when recording image streams of object 106 and/or when displaying select image streams on device 130 and/or live feed 105. This video overlay is for example formatted as tabulated figures that include the performance statistics and/or a graphical representation of the performance of object 106.

In another embodiment, recording device 120 replays recorded image data 119, velocity and position information 126 and annotation data 127 as feed 105 featuring one or more objects 106. Where system 100 is utilized as a training device by a sports team, recording device 120 may be operated to generate output for image feed 105 and/or display device 130 by overlaying velocity and position information 126 and annotation data 127 onto image data 119 for one or more selected athletes. Thus, recording device 120 automatically displays recorded image streams and performance information of the selected athlete. The video overlay and performance information included therein is variable according to sport and/or preference or selection of a user of recording device 120. In one example, live feed 105 may drive a large stadium display during practice to highlight training performance.

In one embodiment, recording device 120 delivers instant replay images or video streams that include overlaid performance information determined from velocity and position information 126 and/or annotation data 127 for the object(s) 106 associated with the selected image data 119.

In another embodiment, recording device 120 generates live image feed 105 by combining a video overlay of performance information selected from velocity and position information 126 and/or annotation data 127 and image data 119. In particular, recording device 120 of this embodiment matches performance information from annotation data 127 to image data 119 for each object 106 to which a camera 110 is assigned.

Recording device 120 may also connect to (or include) a wireless transceiver 140 that communicates with a hand held display and control device 142 to allow a coach to utilize system 100 while on a practice field. Further, transceiver 140 may communicate wirelessly with one or more head-up-display devices, such as glasses 144, worn by athletes to provide real-time display of performance related information and other training aids. Glasses 144 may utilize, for example, Light-guide Optical Element (LOE) technology, such as that employed in Video Eyeglasses manufactured by Lumus Ltd.

Skill—Evaluation and Improvement

Real time position data may be used to measure, evaluate and compare athlete skill parameters such as velocity, acceleration and change of direction agility on predefined drill paths. In addition, using velocity and position information 126 to control cameras 110 to track objects 106 within field 108, skill and performance of athletes represented by objects 106 may be evaluated when performing these predefined drills, such that mechanics of the athlete may be evaluated and corrections made to the athlete's techniques to improve future performance.

Data Only—Performance Evaluation

Figure 2:
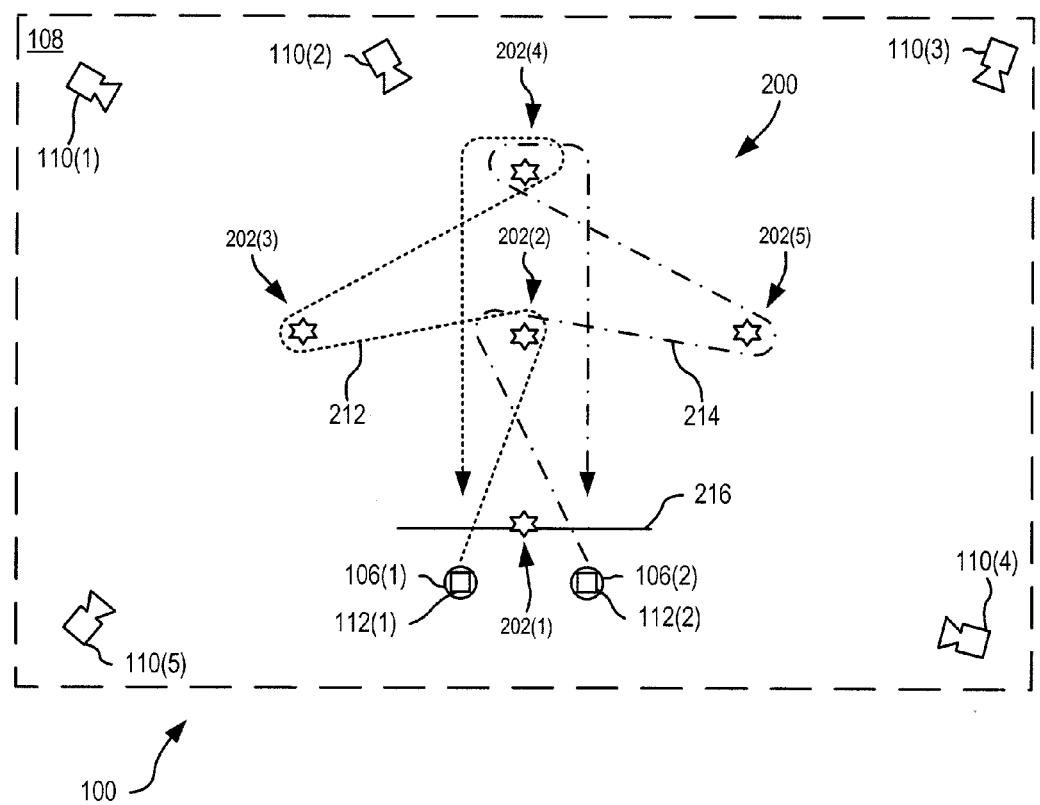
FIG. 2 illustrates use of the system of FIG. 1 for measuring skill and performance of training athletes performing a drill.

FIG. 2 shows use of system 100, FIG. 1, for measuring skill and performance of training athletes performing an arrowhead drill 200 within field 108. Arrowhead drill 200 involves two athletes (represented as objects 106(1) and 106(2)), five cones 202(1)-202(5) placed five yards apart as depicted in FIG. 2, and two discrete paths 212 and 214.

The first athlete (object 206(1)) starts out from a start/finish line 216 on path 212 and the second athlete (object 206(2)) starts on path 214 once the first athlete has reached cone 202(2). By continually or periodically monitoring velocity and position of objects 206 while performing arrowhead drill 200, system 100 may determine agility of each athlete. For example, determining speed, acceleration and change of direction for each athlete may be measured as a continuous function over one or more predefined drill paths to provide significantly more detailed information on the athletes' agility and skill level than by evaluating speed and acceleration as average values between discrete points using fixed measurement devices (such as stop watches, touch pads and photocells), as previously done. The collection of velocity and positional information (i.e., velocity and positional information 126) eliminates the need for mechanical measurement devices along the drill path and allows velocity and acceleration data to be determined at any point along the path(s).

Performance drills are intended to predict the eventual success level of an athlete in real world situations. In the most primitive form, a stop watch collects time from start of the drill to completion to provide a gross measure of overall performance and may be useful as a first pass selection of athletes. However, this simple timing measurement gives no indication of how the athlete performed each element of the drill. Discrete measurement points along the path may be added to provide additional information, but since they are limited to discrete points along the path, this additional information is still limited to average performance measurements of the drill elements.

The collection of continuous data by system 100 provides complete performance measurements, such as velocity and acceleration, at all points along each element of the drill. In football drills, such as arrowhead drill 200 of FIG. 2, these parameters are particularly critical at turning (cutting) points. Continuous data collection allows fine distinction between the performances of multiple athletes. This distinction may be critical in determining how well an athlete should perform in a real world situation. For instance, a first and second athlete may have the same overall time when performing a drill; however, the first athlete may be achieving this time by an ability to cut right and accelerate exceptionally well, while being slow in cutting and accelerating left. In contrast, the second athlete may cut and accelerate equally well to both the right and the left. In real world situations of a football game, the second athlete with balanced ability should consistently outperform the first athlete who is unbalanced, since defenders facing the second athlete will not be able to predict which way the second athlete will choose to cut as the second athlete has equal ability in both directions, whereas the athlete would typically favor his fastest cut direction.

Thus, by monitoring velocity and position information continually (or periodically) for each athlete, weaknesses and strengths of each athlete may be easily measured.

In the simplest form, continuous real time position data collection may be employed on a 40 yard dash. Although existing systems provide total time and split times at discrete points along the path, from which the average velocity and acceleration between the split points can be calculated, these average values are limited by the positions of the discrete points. Since system 100 may collect position information in real time, velocity and acceleration values may be determined as a continuous function, allowing plots of instantaneous velocity and acceleration at any point along the 40 yard path.

The 40 yard dash and arrowhead drill 200 are used as examples and should not be used to limit the scope hereof. The advantages of real time data collection over existing discrete measurement systems hold true for all practice drills in all sports.

Data and Camera Integration—Performance Evaluation & Improvement

Camera control device 104, FIG. 1, may use velocity and position information 126 from object tracking device 102 to automatically aim one or more cameras on one or more athletes performing a drill path such that recording device 120 may record video of the athlete's motion and performance data. For example, recording device 130 may generate one or more displays (e.g., on display 130, video feed 105, handheld device 142 and/or heads-up-display device/glasses 144) showing direction vectors and/or acceleration plots overlaid onto video of the athlete performing the drill to allow a coach to evaluate the athlete's mechanics and performance at specific points on the drill path. The coach may replay this video and data overlay to make determinations between athletes and in coaching methods for athletes to improve their individual performance.

Practice Field—Evaluation and Productivity

Data Only and Camera Integration—Keep Practice Productive

On a practice field it is often difficult, if not impossible, to know where all players are at all times. This is especially true when players have assignments on multiple squads such as offense, defense and any one of the special teams. If the coach cannot find an athlete, that athlete may miss important coaching advice and training. Further, one athlete missing from a training session may prevent training of ten other players on a squad until the missing athlete is found. Much valuable practice time is often lost due to players not being in the right location.

Since system 100 collects real time position information for all objects 106 continually, a coach may determine the location of any athlete by identifying the player (e.g., entering the player's number) to system 100 such that recording device 120 may display the current location of the player to the coach. In one example of operation, a coach enters a player's number into handheld device 142 and recording device 120 displays a plan of field 108 showing the location of the selected player. Optionally, system 100 may be configured and/or operated to display live video imagery of the player's activity to the coach on handheld device 142 by activating one or more cameras 110 to image the current location of the selected player. Thus, through the use of system 100, the coach learns the location of the selected player and can see the activity of that player, thereby allowing an instantaneous decision as to whether to call on him, wait for him or select a substitute.

Data Only—Assignment Verification

Collected, real time position data of an athlete(s) continuous position during a play can be used to determine whether the athlete correctly performed his specific assignment. As an example, consider an offense practicing plays where the receiver routes are of particular interest.

Figure 3:
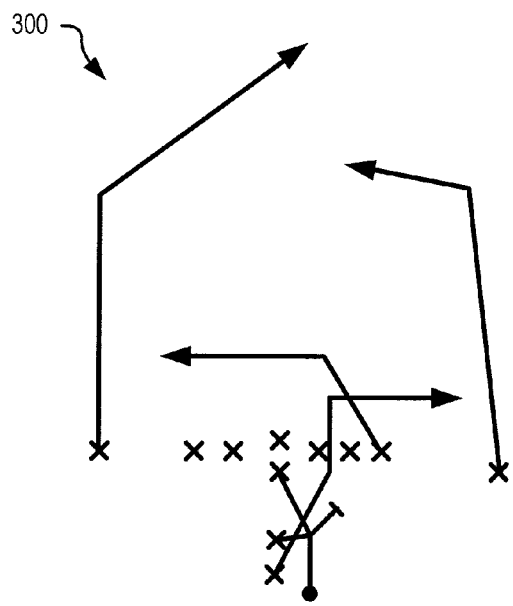
FIG. 3 shows one exemplary Perfect Execution template.

Assignment Verification Operation:

"Perfect Execution" Capture:

11 players may be outfitted with positioning tags so that their exact positions can be recorded as a play is executed. After diagramming the play, the players may walk through the play exactly as it is supposed to be executed. The data from all 11 players is plotted and saved in a play library as a template, such as Perfect Execution template 300, FIG. 3, for later comparison against subsequent executions. For simplicity only the receiver paths are shown in template 300; however, in most cases the paths of all 11 players would be captured, plotted and stored. This can be done for all plays in a playbook and the "Perfect Execution" need only be captured once for each play.

Figure 4:
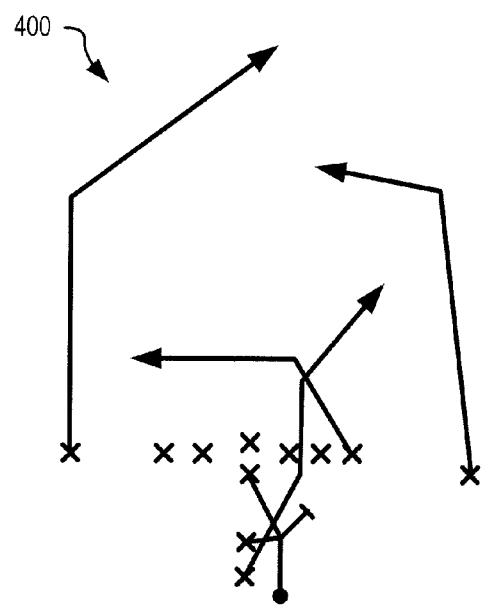
FIG. 4 shows one exemplary plot of data captured during a play.

"Practice Execution" Capture:

The players are told to run a specific play. This play may be executed at walk through speed, half speed or full speed. The real time continuous position of each player is captured as the play unfolds. Immediately following the play, the data for each player is plotted. An example of such a plot is shown in FIG. 4. For ease of illustration, Practice Execution plot 400 shows only the receiver paths; however, in most cases the paths of all 11 players would be captured and plotted.

"Assignment Verification:"

Figure 5:
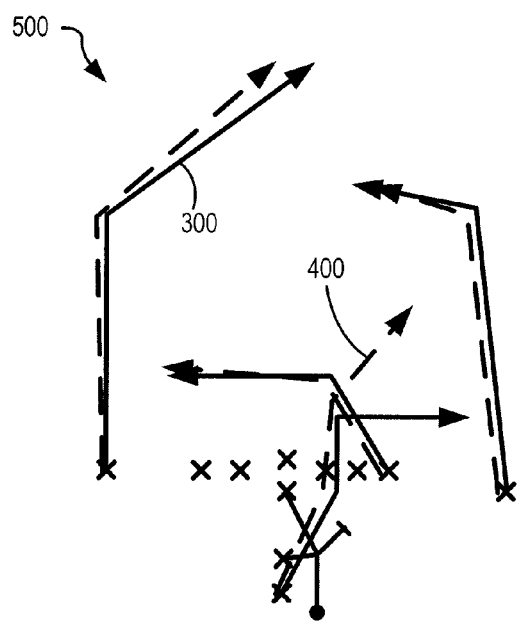
FIG. 5 shows one exemplary overlay of the plot of FIG. 4 and the template of FIG. 3.

The Practice Execution plot 400 is then overlaid on the Perfect Execution template 300 for immediate evaluation by coaches on the field. An example of such an overlay is shown by overlay 500, FIG. 5. The solid lines represent perfect execution template 300 and the dashed lines represent practice execution plot 400. From this example, it is immediately obvious that the tight end and wide receivers ran their assigned routes reasonably close to design while the tailback clearly deviated from his assigned route.

"Overlay Automation:"

For practical implementation, Perfect Execution template 300 and Practice Execution plot 400 overlay automatically. Furthermore, the overlay may be independent from where the data for each was collected. For example, Perfect Execution template 300 may be collected in a gym while Practice Execution plot 400 may be collected on a practice field days or even years later. In addition, successive plays may originate from different points on the practice field, and they could be moving in either direction.

Automatic overlay is accomplished by selecting two stable reference points whose relative starting positions to each other are known. For instance, in both Perfect Execution template 300 and Practice Execution plot 400, the position of the right tackle is known and stable relative to the position of the left tackle. Therefore, this relationship can be used in establishing the overlay starting point.

Data and Camera Integration—Mechanics & Performance Evaluation

Real time position data is used to aim a camera(s) automatically at specific athletes of interest during a practice play execution to record video of the execution. The number of athletes videoed is limited only by the number of cameras. The video can be viewed in real time, while the play is being executed, or saved and reviewed later.

Real Time Video & Performance Data

The video stream from the camera is transmitted to a handheld or tablet computer being held by a coach on the field. The coach selects the player of interest on the screen before the play is executed. While the play is being executed, the camera isolates on this player and the video is streamed to the handheld for the coach to view in real time. As the player moves on the field a yellow line indicating the path traveled is laid down on the image of the field. A data window on the screen also indicates the current velocity and acceleration of the player.

Replay of Video & Performance Data

In addition to streaming the video to the handheld, the video is also streamed to disk. The stored video can be used on the field by the coach for instant replay, which can be used in coaching the player. The replay video can be stopped at any point to freeze the action and highlight specific situations. The coach can also access the velocity and acceleration of the player at any point by touching the screen on the yellow path indication line.

Post Analysis of Video and Performance Data

All continuous position, velocity, acceleration and path data, as well as video, from a practice session can be stored for post analysis. Successive plays can be compared to isolate what performance elements contributed to the success or failure of a particular play execution. For instance, in the case of a wide receiver running a route and being covered by a defender.

Post Analysis Use of Video:

Video can be used to analyze the receiver's body motion while running his route and distinguish between moves "fakes" which are successful in confusing a defender, resulting in a successful play, from moves which did not confuse the defender resulting a an unsuccessful play.

Post Analysis Use of Data Parameters:

Data such as velocity and acceleration at any point along the path traveled can be compared to identify the precise point at which burst of acceleration is particularly successful in getting distance between the receiver and the defender.

While the examples above involve an offensive play, identical situations exist for defensive plays as well as all special teams plays.

Integration of Real Time Data with Audio Feedback—Training & Task Execution

The collection of continuous real time position data can be used in conjunction with an "in helmet" audio system to assist players in learning and perfecting new tasks. The audio system is mounted in the player's helmet in stereo fashion with a miniature speaker at the left and right ears. The speakers operate independently allowing specific information to be communicated to the player, in real time, through variations in tone and volume. The following are examples of how this might be used to train various player positions but the same principles could be applied to all positions in learning and perfecting new tasks.

Audio Feedback—Quarterback Example:

To be an effective passer, a quarterback must know how much time he has in "the pocket" before he must get rid of the ball or run. The most basic parameter is time, which is measured in seconds (typically 3.5 or less). Failure to wait as along as possible could mean making a bad decision or throwing before a receiver has had time to get open. However, waiting 1 ms too long could result in a sack or career-ending injury.

Continuous real time data in conjunction with audio feedback can be used in helping a quarterback to learn the optimal time in the pocket. Real time position data is used to determine when the quarterback is located in the pocket. As soon as he is in position a timer start and a beeping sound is sent to the speakers in his helmet. This beeping increases in frequency as time expires. The frequency continues to increase until the maximum time has elapsed and the beeping becomes a steady tone.

In the real world, the maximum amount of time a quarterback has in the pocket may be cut short by defenders reaching him more quickly than anticipated. To be effective in this situation a quarterback must learn to "feel" the pressure of defenders. Defensive pressure usually comes from the left or right side and in this case the quarterback must sense the pressure through peripheral vision. Since he is focused down field looking for potential receivers this can be a difficult skill to master. By tracking the real time position of the defenders their proximity to the quarterback is easily determined. To aid the quarterback in learning to "feel" this pressure the beeping frequency can be increased more rapidly to reflect the decreasing available time in the pocket and the volume of the right or left speaker can be increased to indicate the specific direction the pressure is coming from.

Audio Feedback—Receiver Example:

For a receiver to be effective, he must be where the quarterback expects him to be. The most basic element of this is running the proper route. Continuous real time position data in conjunction with audio feedback can be used to help the receiver learn his routes quickly and accurately so that he runs them the same every time.

When the receiver first begins his route, there is tone of equal volume in both speakers. As he moves along the path, the system senses his position and slowly increases the volume in the ear on the side to which he will eventually cut. Upon arriving at the cut point, the volume in the speaker on the side of the cut hits a peak and the speaker on the opposing side shuts down completely.

The second element of being in the right place, and eluding defenders, involves running the various legs of the route at different speeds. In this instance, the tone in the example above would be replaced by a beeping sound. The frequency of the beeping indicates the speed at which the receiver should be running. In a simple case, a low frequency would represent a jogging speed, a medium frequency would represent a medium speed run and a high frequency beeping would present full speed. The system controls the beeping frequency by sensing what leg of a route the receiver was on and delivering the preprogrammed speed message. In an alternate embodiment, the beeping may have a frequency based upon a desired cadence for the athlete, thereby indicating the desired running speed.

Both messages (speed & direction) can be delivered to the receiver by employing the volume and beeping frequency described above simultaneously. The beeping frequency indicates the speed to run and the volume of the beeping in the right or left ear indicates the direction to turn.

Integration of Real Time Data with Visual "Heads-up" Feedback—Training & Task Execution The collection of continuous real time position data can be used in conjunction with "heads up" technology to assist players in learning and perfecting new tasks. The heads-up technology consists of a pair of transparent glasses 144 (FIG. 1), worn by the player, which have the capability to accept wireless data and project this data in the form of images, which appear to the player to be at some distance in front of the glasses.

Visual Heads-up Feedback—Quarterback Example:

Time in the Pocket:

To be an effective passer, a quarterback must know how much time he has in 'the pocket' before he must get rid of the ball or run. The most basic parameter is time, which is measured in seconds (typically 3.5 or less). Failure to wait as along as possible could mean making a bad decision or throwing before a receiver has had time to get open. However, waiting 1 ms too long could result in a sack or career ending injury.

Continuous real time data in conjunction with heads-up technology can be used in helping a quarterback to learn the optimal time in the pocket. Real time position data is used to determine when the quarterback is located in the pocket. As soon as he is in position, a timer starts and bar graphs located in both the far right and left corners of his vision begin growing. When there is 0.5 seconds remaining the graphs begin blinking and when time has expired, they turn solid red.

In the real world, the maximum amount of time a quarterback has in the pocket may be cut short by defenders reaching him more quickly than anticipated. To be effective in this situation a quarterback must learn to "feel" the pressure of defenders. Defensive pressure usually comes from the left or right side and in this case, the quarterback must sense the pressure through peripheral vision. Since he is focused down field looking for potential receivers, this can be a difficult skill to master. By tracking the real time position of the defenders, their proximity to the quarterback is easily determined. To aid the quarterback in learning to "feel" this pressure the bar graphs can be increased more rapidly to reflect the decreasing available time in the pocket. In addition, the system can sense the specific position of the defenders and they can be represented by dots that start out at the far most sides of the glasses and move toward the center as the defenders get closer. When the defender dot reaches the center of the vision area, the defender has reached the quarterback.

Receiver Looks:

In any passing play, a quarterback has multiple receivers to select from and a limited time to make the best selection. The process of deciding which receiver to throw to is referred to as "receiver looks". The most effective quarterbacks are those who methodically move through these looks to find the best receiver to throw to. Typically, there will be a primary look, the receiver the ball is intended to go to, a secondary look, the receiver the quarterback will consider if the primary is tightly covered and a safety valve. The safety valve is a receiver positioned such that the quarterback can dump the ball off when he has reached his maximum time in the pocket (described above). Note that a quarterback typically only has 1.2 to 1.5 seconds to evaluate each of his receivers so this is not an easy skill to perfect, especially under defensive pressure.

Continuous real time data in conjunction with heads-up technology can be used in helping a quarterback learn to rotate methodically through his available receivers. As the quarterback drops back into the pocket, the dynamic position of the primary receiver appears as a dot in his vision. Since the system is sensing the actual position of the primary receiver this dot represents the actual, relative position of the receiver. If the receiver starts out on the left side and runs straight up the field, then the dot will start in the bottom left hand side of the vision and move up the left side of the vision. If the receiver runs across the middle then the dot will start out in the bottom left and move up and left to right through the vision. As an aide to help the quarterback rotate at the right time, the receiver dot begins to blink at programmed time (say 1 sec). At a preprogrammed time (say 1.5 sec) the primary receiver dot turns off and the secondary receiver dot turns on and functions in the same manner as the primary receiver dot. Following the second interval (say 1.5 sec or total of 3 sec), the safety receiver dot turns on. Optionally, dots corresponding to multiple potential receivers are shown simultaneously in the quarterback's vision, allowing the quarterback to select the best receiver (e.g., the receiver in a most desired position) to throw to, from multiple options.

Team Position Reads:

Real time position of all or select members of a team may also be represented with heads-up technology, enabling a player (e.g., the quarterback) to determine when other players are in or approaching a desired position. For example, position of players involved in a predetermined play may appear as dots in the quarterback's vision. When the dots achieve or approach a desired formation, indicating that players are in position for or moving into position for the play, the quarterback may initiate the play.

Combining Time in the Pocket and Receiver Reads:

As a quarterback's training progresses the time in pocket feedback and receiver look elements can be integrated to provide the quarterback with maximum real time feedback to become a more effective and efficient passer.

Simulated Use of Heads-Up Feedback

Once data has been captured while using this system in practice with real receivers and real defenders, it can be replayed at any time. This allows the quarterback to practice and experience the live situation without all of the other players being present thus allowing them to work on perfecting their own individual roles. This is essentially a video game where the quarterback is an active participant and the actions of the receivers and defenders are derived from data of his actual teammates. This allows players in skill positions, such as quarterbacks, to maximize the amount of time they spend perfecting their role, under life like conditions, without requiring the other 21 players to be present. This video game like ability yields an unprecedented advance in the training of skill position players.

Visual Heads-Up Feedback—Receiver Example:

Route Definition:

In this situation the heads-up glasses display is used much like the display on a GPS. The receiver is able to look right through the transparent glasses, but a line indicating the specified route would be projected in front of him. The system continuously senses the receiver's position and as he traveled down each leg of the route, the path would get shorter and shorter until he reached a turning, or cutting, point. As soon as he made his cut, the next leg of the route would turn upward indicating forward motion in that direction.

Route Speed:

Each leg of a route may have a different ideal speed and in some cases there may even be multiple speeds per leg. As the receiver moves along the path, specified by the route definition method described above, the ideal speed in feet/sec is projected in his field of view. The system continuously monitors his current speed and displays this next to the ideal speed. The system monitors the athlete's performance in real time and may provide visual indications to the athlete when the athlete meets certain desired criteria, or when those criteria are not being met by the athlete. For example, if the athlete needs to speed up then his actual speed may be projected in green and if he needs to slow down then it may be projected in red.

Game Time—Coaching

Data Only—Assignment Verification

Assignment verification can be employed in a game situation in exactly the same way it is employed during practice sessions. This provides coaches with real time feedback as to which players are performing their assignments accurately and consistently.

Data Only—Fatigue Analysis

Various parameters such as time on the field and distance traveled may be tabulated and used to determine when a player's effectiveness may be diminishing.

"Time on the Field"

The total amount of time a player is on the field during a quarter, half or game can be determined by accumulating time when the player is located in the region of play defined by the playing field and both end zones. This parameter can be made even more relevant by associating the time accumulation with the playing clock such that time on the field is only accumulated when the game clock is running.

"Distance Traveled"

In many skill positions, such as running backs, defensive backs and receivers, total distance traveled by the athlete may be a more accurate determinant of fatigue than time on the field. The total distance traveled by an athlete during a quarter, half or game can be determined by accumulating distance traveled when the player is located in the region of play defined by the playing field and both end zones.

Data and Camera Integration—Opposition Evaluation

Real time position data is used to aim a camera(s) automatically at the area "around" a specific athlete of interest. By aiming a camera at the area around a specific athlete it is possible to determine how the opposition is responding to specific actions of the athlete of interest. For instance, by aiming a camera at the area around a wide receiver the defensive backfield rotations and/or assignments of the opposition can easily be determined.

Figure 6:
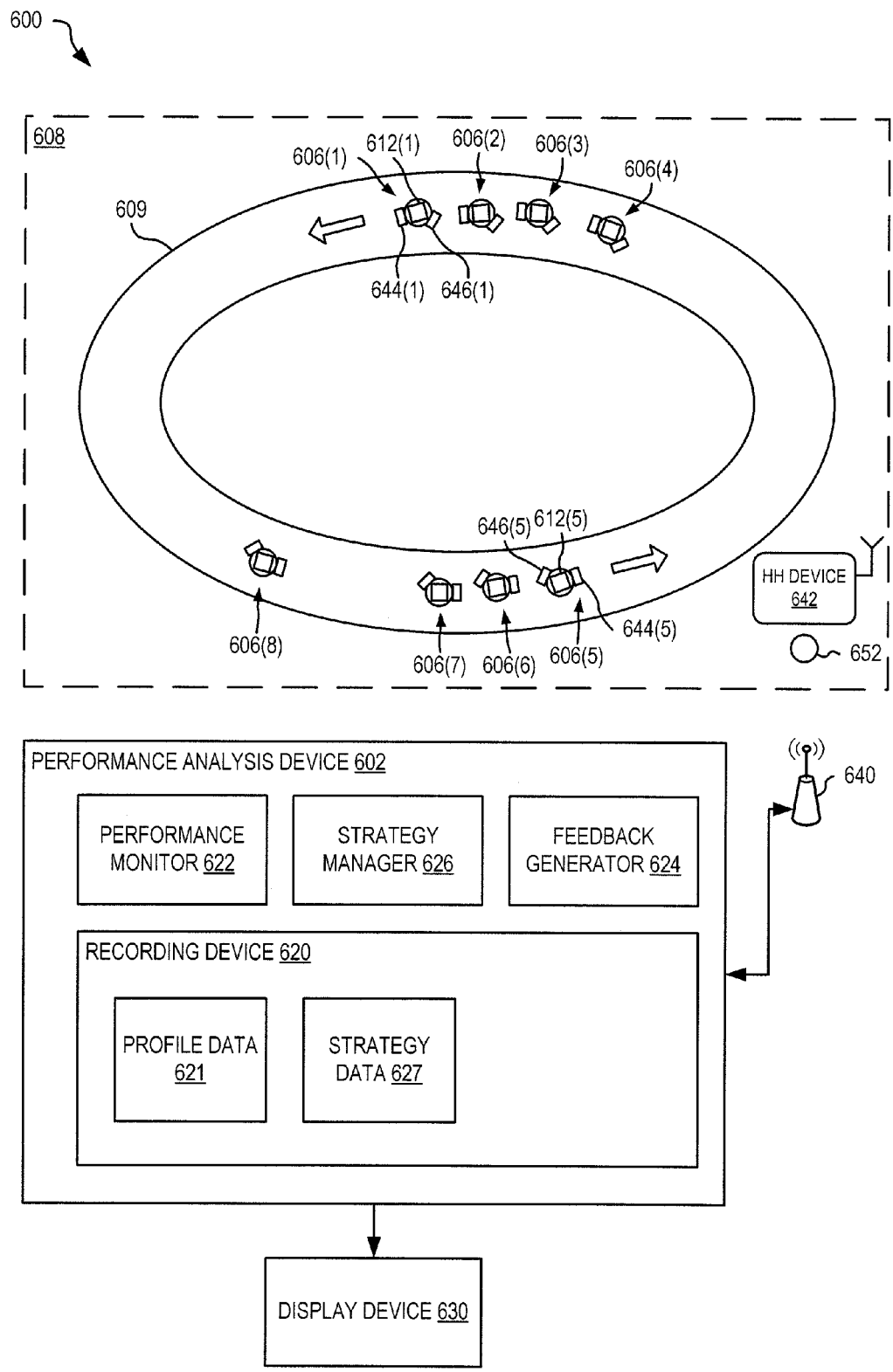
FIG. 6 shows one exemplary system for providing performance feedback, in an embodiment.

FIG. 6 shows one exemplary system 600 for providing performance feedback. For purposes of example, system 600 is described below with respect to athletes. However, it will be appreciated that system 600 is not limited to use by athletes or an athletic team (including a coach), but may provide beneficial performance feedback to any participant in a field of play.

System 600 includes a performance analysis device 602 that determines a location of each of a plurality of athletes 606 within an operational field 608. In the example of FIG. 6, athletes 606 are formed into two pursuit teams that include athletes 606(1-4) and athletes 606(5-8), respectively, that race around circuit 609 in a direction indicated by arrows. Each athlete 606 wears a location device 612 that is used by performance analysis device 602 to determine the location of the athlete, a biometric sensing unit 646 that senses biometric information of the athlete, and a feedback device 644 that provides feedback from performance analysis device 602 to the athlete. The biometric information sensed by biometric sensing unit 646 may include one or more of: body temperature at one or more locations, heart rate, blood oxygen levels, hydration level, respiratory rate, perspiration salinity level, blood sugar levels, and other blood analysis results. For example, Cygnus Inc.'s GlucoWatch checks glucose levels every 20 minutes by sending tiny electric currents through the skin. Biometric sensing unit 646 may sense other biometric information without departing from the scope hereof Feedback device 644 may represent one or more of a visual display, such as a liquid crystal display (e.g., a watch and a bicycle handlebar display unit) and a HUD incorporated within glasses (e.g., glasses 144, FIG. 1) and/or a helmet, an audio output unit that generates audio signals such as beeps, tones and verbal information, and an actuator that provides movement (tactile) feedback. Where the athlete is taking part in a sport that utilizes equipment that is ridden, such as a bicycle, feedback device 644 may be attached to the equipment or the athlete. Performance analysis device 602 utilizes a wireless transceiver 640 to send feedback information to each feedback device 644, to receive biometric information from biometric sensing units 646, and to receive location information from location units 612.

Performance analysis device 602 includes a performance monitor 622 that utilizes real time location information from location units 612 and biometric feedback information from biometric sensing units 646 to determine, for each athlete 606, performance that includes one or more of location, velocity, stress level, and fatigue level. Performance monitor 622 may also generate and maintain profile data for each athlete, shown as profile data 621 stored within recording device 620 of performance analysis device 602. Profile data 621 may include, for each athlete, historical performance such that current and future performance of the athlete may be predicted. For example, if a particular athlete finished a four-thousand meter training race in the morning, a lighter level of afternoon training may be expected for that athlete and performance analysis device 602 may not push the athlete as hard as another athlete who was resting that morning.

Recording device 620 may generate a live feed and allow interaction with a user through a display device 630.

In the example of FIG. 6, each athlete 606 receives feedback for his team. For example, each athlete 606(1-4) receives feedback including location, stress and fatigue levels, for themselves and each other. Similarly, each athlete 606(5-8) receives feedback including location, stress and fatigue levels, for themselves and each other. Feedback generator 624 may also provide feedback defining each team performance with respect to the other. For example, in the pursuit illustrated in FIG. 6, timing between each last athlete of each team (i.e., athletes 606(4) and 606(8)) may be provided to each athlete 606. As the order of each team changes through rotation, performance analysis device 602 automatically identifies the 'last' man of the team. Performance monitor 622 and feedback generator 624 may also provide each team with relative position information of each team member, such that a current leader of the team becomes aware when the last member begins to fall too far behind. For example, feedback device 644 displays four green dots or blips to indicate team members in position, and a red dot or blip to indicate a team member falling behind. In one aspect, the leader of a track cycling team becomes aware (via performance monitor 622 and feedback generator 624) that the last man of the team is struggling to keep pace and may thus modify the team's pace to prevent exhaustion of the last man, in hopes of bettering the team's collective race result.

In another example, a quarterback receives feedback, indicating a projected fatigue level for potential receivers, allowing an informed choice as to which receiver to select for a particular play. Similarly, the quarterback may receive fatigue information for defenders such that potential weaknesses may be reduced or at least identified at the last second prior to the snap of the football.

Each athlete 606 may receive feedback indicating the location of other athletes relative to himself, particularly athletes not directly in his current field of view. Further, each athlete may receive feedback relating to their entire team, based upon processing of data by performance analysis device 602. For example, where a player in a football team is recovering from high impact in a previous play, other team members will be aware of this through feedback from performance analysis device 602.

Biometric sensing units 646 may include one or more accelerometers that measure impact to athlete 606 and movement of the athlete. In one example, these biometric sensors measure cadence of the athlete running such that performance monitor 622 may determine stride length (e.g., based upon measured cadence and speed determined from location information).

Performance analysis device 602 may also monitor athletes 606 while resting between training exercises, such that profile data 621 for each athlete includes recovery rates.

Performance analysis device 602 may include a strategy manager 626 that creates and/or utilizes strategy data 627 stored within recording device 620. In one example, strategy data 627 represents plays (e.g., Perfect Execution Template 300, FIG. 3) in an American football game, or practice session. Strategy manager 626 may define criteria (e.g., paths and speeds) for one or more players in the play and feedback generator 624 sends these criteria to feedback devices 644 of relevant players. Performance monitor 622 may monitor movement of each player (e.g., using location units 612) and provide feedback, via feedback generator 624, indicating how well, or not, each player conforms to the suggested path and speed. Feedback generator 624 may also provide, in real-time, corrective moves and instructions to players that do not maintain the desired criteria.

FIG. 6 also shows a coach 652 of athletes 606 utilizing a hand held device 642 that wirelessly interacts, via transceiver 640, with performance analysis device 602. Hand held device 642 may include a processor, a memory, an input device and a display, such as found in an Apple™ iPad. Device 642 allows coach 652 to view live performance information determined by performance analysis device 602 for athletes 606, and feedback that is sent automatically to the athletes from feedback generator 624. Coach 652 may provide input to object tracking device, via hand held device 642 and transceiver 640, to adjust the level of feedback provided by performance analysis device 602.

In an embodiment, coach 652 receives 'alarm' messages from performance analysis device 602, via wireless transceiver 640 and hand held device 642, indicating athletes that have one or more of: high stress levels, high fatigue levels, high temperatures, and other abnormal biometric information. Coach 652 may then make informed decisions to rest athletes prior to potential injuries or life threatening conditions.

Changes may be made in the above methods and systems without departing from the scope hereof. For example, the athletes referenced above may represent any type of participant within an operational field or field of play. Performance analysis device 602 for example provides biometric information to and of any "team". By tracking and reporting biometric data of team members, performance analysis device 602 allows team members to monitor one another, and/or allows an instructor, coach or supervisor to monitor each team member. In one aspect, performance analysis device 602 allows commercial divers, astronauts or fighter pilots to monitor one another for signs of panic (e.g., increased respiration and heart rate) or distress even when out of sight. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for providing feedback to at least one of a plurality of participants in a real field of play of a sport, comprising:

a single performance analysis device having a processor capable of:

continuously determining real-time position information of each of the plurality of participants concurrently playing the sport in the real field of play, determining real-time performance information of each of the plurality of participants based on instantaneous velocity, instantaneous acceleration, and change of direction at any point of a predefined path, wherein the instantaneous velocity, instantaneous acceleration, and change of direction are based upon a continuous function of the real-time position information; and at least one output device having a processor capable of providing real-time feedback to the at least one participant based upon the performance information for the at least one participant and another of the plurality of participants concurrently playing the sport wherein the real-time feedback comprising desired speed and actual speed of the at least one participant on a route; and the actual speed being displayed by (a) displaying the route in a first color if the participant's speed is faster than the desired speed and (b) displaying the route in a second color if the participant's speed is slower than the desired speed.

2. The system of claim 1, wherein determining the real-time information includes obtaining biometrics of each of the participants, the biometrics comprising one or more of body temperature at one or more locations, heart rate, blood oxygen levels, hydration level, respiratory rate, perspiration salinity level, and blood sugar levels.

3. The system of claim 1, the real-time feedback comprising, a desired performance of the participant during a play in the sport.

4. The system of claim 1, the real-time feedback provided to each of the plurality of participants comprising (a) real-time performance information of said participant and (b) real-time performance information of at least one other of the plurality of participants in the real field of play.

5. The system of claim 4, the real-time performance information of the at least one other participant comprising a distress level.

6. The system of claim 1, the output device comprising a heads-up display worn by the at least one participant for displaying the real-time feedback.

7. The system of claim 1, the at least one output device comprising a plurality of heads-up displays, each of the heads-up displays worn by a separate one of the participants, wherein each of the heads-up displays presents different real-time feedback specific to each participant.

8. The system of claim 6, the real-time feedback comprising a desired route, that is projected on the heads-up display, that the at least one player is to perform.

9. The system of claim 6, the feedback comprising visual simulation of at least one participant based upon data derived from previously recorded performance information of the other plurality of players.

10. The system of claim 1, the output device comprising an audio output unit co-located with the at least one participant, the feedback comprising an audio signal.

11. The system of claim 10, the audio signal comprising a stereo tone wherein left and right volume of the tone indicates a corresponding direction to be followed by the participant.

12. The system of claim 10, the audio signal comprising a tone having a beeping frequency that conveys desired speed of the participant.

13. The system of claim 10, the audio signal comprising a tone having a beeping frequency that conveys situational pressure to the participant, wherein the beeping frequency increases as the situational pressure increases, the situational pressure being associated with at least one other participant concurrently playing the sport.

14. The system of claim 1, the output device comprising at least one wirelessly controlled actuator co-located with the at least one participant for providing tactile feedback.

15. A method for providing feedback to at least one of a plurality of participants in a real field of play for a sporting event, comprising:

determining, within a performance analysis device, continuous successive locations of each of the plurality of participants concurrently participating within the real field of play;

determining, within the performance analysis device, performance of the one participant based upon the successive locations of the participant, wherein the performance is based on instantaneous velocity, instantaneous acceleration, and change of direction at any point of a predefined path, wherein the instantaneous velocity, instantaneous acceleration, and change of direction are based upon a continuous function of the continuous successive locations; and providing real-time feedback to the participant, from performance analysis device, based upon the determined performance of at least one of the participants concurrently participating within the real field of play wherein the real-time feedback comprising desired speed and actual speed of the at least one participant on a route; and the actual speed being displayed by (a) displaying the route in a first color if the participant's speed is faster than the desired speed and (b) displaying the route in a second color if the participant's speed is slower than the desired speed.

16. The method of claim 15, wherein the determined performance comprises at least one of location, velocity, acceleration, and agility.

17. The method of claim 15, further comprising generating, at the performance analysis device, one or both of audio and visual signals as the feedback.

18. The method of claim 17, further comprising:

generating, at the performance analysis device, the visual signals that simulate other participants in the real field of play based upon recorded performance of the participants; and displaying the visual signals in a heads-up-display worn by the participant.

19. The method of claim 18, further comprising simulating situational pressure placed upon the participant by visually emulating pressure in the form of at least one of a pressure graph and opponent position.

20. The system of claim 1, the feedback being indicative of dynamic changes within a predetermined situation of the sport, the dynamic changes being based upon changes in the location of one or more of the plurality of participants.

21. The method of claim 15, the feedback being indicative of dynamic changes within a predetermined situation of the sport, the dynamic changes being based upon changes in the location of one or more of the plurality of participants.

22. The system of claim 1, the performance information including both the location and the biometrics of each participant, the real-time feedback including fatigue of said each of the participants, wherein the fatigue is based on at least one of time on field and total distance traveled of said each of the participants.

23. The method of claim 15, the performance information including both the location and the biometrics of each participant, the real-time feedback including fatigue of said each of the participants, wherein the fatigue is based on at least one of time on field and total distance traveled of said each of the participants.

* * * * *